(12) United States Patent
Brown et al.

(10) Patent No.: US 7,615,368 B1
(45) Date of Patent: Nov. 10, 2009

(54) MICROARRAYS OF POLYPEPTIDES

(75) Inventors: Patrick Brown, Stanford, CA (US); Tidhar Shalon, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1111 days.

(21) Appl. No.: 09/550,303

(22) Filed: Apr. 14, 2000

Related U.S. Application Data (63) Continuation-in-part of application No. 09/356,322, filed on Nov. 24, 1998, now Pat. No. 7,442,499, which is a continuation of application No. 08/688,488, filed on Jul. 30, 1996, now Pat. No. 7,323,298, which is a continuation-in-part of application No. 08/514,875, filed on Aug. 14, 1995, now Pat. No. 7,378,236, which is a continuation-in-part of application No. 08/477,809, filed on Jun. 7, 1995, now Pat. No. 5,807,522, which is a continuation-in-part of application No. 08/261,388, filed on Jun. 17, 1994, now abandoned.

(51) Int. Cl.
*C12M 1/36* (2006.01)
*C07K 5/00* (2006.01)
*B01L 3/02* (2006.01)

(52) U.S. Cl. .................. 435/283.1; 435/287.2; 530/333; 530/334; 422/100

(58) Field of Classification Search ................. 436/518, 436/532; 530/300, 387.1; 435/287.2, 287.9, 435/7.1
See application file for complete search history.

(56) References Cited

U.S. PATENT DOCUMENTS

| | | | |
|---|---|---|---|
| 3,555,143 A | | 1/1971 | Axen et al. |
| 3,646,346 A | | 2/1972 | Catt ............................ 250/83 |
| 4,591,570 A | * | 5/1986 | Chang ........................ 435/7.24 |
| 5,143,854 A | | 9/1992 | Pirrung et al. .............. 436/518 |
| 5,252,743 A | * | 10/1993 | Barrett et al. ............. 548/303.7 |
| 5,324,633 A | | 6/1994 | Fodor et al. ..................... 435/6 |
| 5,667,976 A | * | 9/1997 | VanNess et al. ................ 435/6 |
| 5,677,195 A | * | 10/1997 | Winkler et al. .............. 436/518 |
| 5,807,522 A | | 9/1998 | Brown et al. .................. 422/50 |
| 5,843,767 A | * | 12/1998 | Beattie .................... 435/287.1 |

FOREIGN PATENT DOCUMENTS

| | | | |
|---|---|---|---|
| GB | 2099578 A | * | 12/1982 |
| WO | WO 97/42507 | | 11/1997 |
| WO | WO 00/12575 | | 3/2000 |
| WO | WO 00/47317 | | 8/2000 |

OTHER PUBLICATIONS

Georffrey Zubay,Biochemistry,Wmc.Brown Publishers,1988.*

(Continued)

*Primary Examiner*—B J Forman
(74) *Attorney, Agent, or Firm*—Bozicevic, Field & Francis LLP; Pamela J. Sherwood (57) ABSTRACT

Microarrays of polypeptides on a solid support are provided. The microarray compositions find use in the multiplexed detection and quantitation of ligands, e.g. antigens or antibodies, in a miniaturized format. The substrate is used for detecting binding of ligands to a plurality of polypeptides for screening and diagnostic purposes.

2 Claims, 6 Drawing Sheets

OTHER PUBLICATIONS

Abouzied et al. (1994), "Simultaneous Screening of Fumonisin $B_1$, Aflatoxin $B_1$, and Zearlaenone by Line Immunoblot: A Computer Assisted Multianalyte Assay System." *Journal of AOAC International*, vol. 77(2):495-500.

Bohlander et al. (1992), "A Method for the rapid Sequence-Independent Amplification of Microdissected Chromosomal Material." *Genomics*, vol. 13:1322-1324.

Catt et al. (1967), "A Solid Phase Disc Radioimmunoassay for Human Growth Hormone." *Journal of Laboratory and Clinical Medicine*, vol. 70(5):820-830.

Drmanac et al. (Jun. 11, 1993), "DNA Sequence Determination by Hybridization: A Strategy for Efficient Large-Scale Sequencing." *Science*, vol. 260:1649-1652.

Fodor et al. (Feb. 15, 1991), "Light-Directed, Spatially Addressable Parallel Chemical Synthesis." *Science*, vol. 251:767-773.

Khrapko et al. (1991), "A Method for DNA Sequencing Hybridization wth Oligonucleotide Matrix." *DNA Sequence*, vol. 1:375-388.

Nelson et al. (May 1993), "Genomic Mismatch Scanning: A new Approach to Genetic Linkage Mapping." *Nature Genetics*, vol. 4:11-18.

Riles et al. (May 1993), "Physical Maps of the Six Smallest Chromosomes of *Saccharomyces cerevisiae* at a Resolution of 2.6 Kilobase Pairs." *Genetics*, vol. 134:81-150.

Schena et al. (May 1992), "HD-Zip Proteins: Members of an *Arabidopsis* homeodomain Protein Superfamily." *Proc. Natl. Acad. Sci. USA*, vol. 89:3894-3898.

Southern et al. (1992), "Analyzing and Comparing Nucleic Acid Sequences by Hybridization to Arrays of Oligonucleotides: Evaluation Using Experimental Models." *Genomics*, vol. 13:1008-1017.

Frank, Ronald (1992), "Spot-Synthesis: An Easy Technique for the Positionally Addressable, Parallel Chemical Syntheses on a Membrane Support." *Tetrahedron*, vol. 48(42):9217-9232.

Gruber et al. (Jun. 16-21, 1992), "Light-Directed Combinatorial Peptide Synthesis." *Proceedings of the 12th American Peptide Symposium*, pp. 489-491.

Holmes et al. (1995), "The Use of Light-Directed Combinatorial Peptide Synthesis in Epitope Mapping." *Biopolymers (Peptide Science)*, vol. 37:199-211.

Jacobs et al. (Jan. 1994), "Combinatorial Chemistry-Applications of Light-Directed Chemical Synthesis." *Tibtech Library*, vol. 12:19-26.

* cited by examiner

Fc h. IgG

Flag

FIGURE 8

MICROARRAYS OF POLYPEPTIDES

CROSS-REFERENCE TO RELATED APPLICATION

This application claims the benefit of priority to provisional application No. 60/129,449, filed Apr. 15, 1999; and is a continuation-in-part of U.S. patent application Ser. No. 09/356,322 filed Nov. 16, 1998, which is a continuation of U.S. patent application Ser. No. 08/688,488 filed Jul. 30, 1996, which is a continuation-in-part of U.S. patent application Ser. No. 08/514,875 filed Aug. 14, 1995, which is a continuation-in-part of U.S. patent application Ser. No. 08/477,809, filed Jun. 7, 1995, now issued as U.S. Pat. No. 5,807,522; which is a continuation-in-part of U.S. patent application Ser. No. 08/261,388, filed Jun. 17, 1994, and now abandoned.

FIELD OF THE INVENTION

This invention relates to methods and apparatus for fabricating microarrays of biological samples, and the uses thereof.

BACKGROUND OF THE INVENTION

Life and development of all organisms are determined by molecular interactions, e.g. between DNA and proteins, proteins and proteins, or proteins and small molecules. Among these, protein-protein interactions play an especially important role, for example with the interactions between antibodies and antigens, receptors and peptide- or protein-hormones, enzymes and substrates or inhibitors. Many of the best-selling drugs either act by targeting proteins or are proteins. In addition, many molecular markers of disease, which are the basis of diagnostics, are proteins.

The development of techniques and reagents for high throughput protein analysis has been of great interest. In particular, the increasing knowledge of DNA sequence in organisms of interest has spurred interest in protein expression analysis. There is now a rapidly growing awareness of just how important proteomics is to understand and organize the human genome. Information about the complement of proteins present in a cell is a key to accelerate the discovery of medically important proteins and the genes from which they derive.

Genomics establishes the relationship between gene activity and particular diseases. However most disease processes are manifested not at the level of genes, but at the protein level. There is often a poor correlation between the level of activity of different genes and the relative abundance of the corresponding proteins. Also a protein and its post-translational modifications are not directly encoded for by the same gene, therefore the complete structure of individual proteins cannot be determined by reference to the gene alone.

Assays directed towards protein binding can be used for the quantitation of protein expression; the determination of specific interactions; to determine the presence of ligands for a protein, and the like. Methods of quantitating proteins in a sample by determining binding to a cognate antibody are known in the art.

For example, solid-phase radioimmunoassay (RIA) of antigens or antibodies in a serum sample are well known. Catt et al. have reported such techniques on the surface of plastic tubes (U.S. Pat. No. 3,646,346) and plastic discs (J. Lab. & Clin. Med., 70: 820 (1967). In such techniques, an excess of specific antibody is first adsorbed to a support surface. Then, the sample to be assayed is immunologically reacted with such surface in a sandwich or competitive binding technique. In the competitive binding technique, illustrated in U.S. Pat. No. 3,555,143, the concentration of antigen to be determined and a known quantity of radioactively tagged antigen are immunologically reacted with the antibody-adsorbed surface. The labeled antigen bound to the antibody on the surface is then quantitated to determine indirectly the total quantity of antigen in the original sample. In the sandwich technique, serum containing an unknown concentration of antigen is immunologically reacted with the antibody-containing surface. Then in a following step, the bound antigen is incubated with labeled antibody and the amount of immunologically bound, labeled antibody is subsequently measured.

The development of high-throughput, parallel systems for protein analysis are of great interest, particularly where the analysis can use small amounts of material for analysis. Preferably such systems provide for the use of complex molecules with high binding affinity for their ligands, such as antibodies, protein receptors, and the like.

LITERATURE

Publications of interest include: Abouzied, et al., Journal of AOAC International 77(2):495-500 (1994). Bohlander, et al., Genomics 13:1322-1324 (1992). Drmanac, et al., Science 260:1649-1652 (1993). Fodor, et al., Science 251:767-773 (1991). Khrapko, et al., DNA Sequence 1:375-388 (1991). Kuriyama, et al., An Isfet Biosensor, Applied Biosensors (Donald Wise, Ed.), Butterworths, pp. 93-114 (1989). Lehrach, et al., Hybridization Fingerprinting in Genome Mapping And Sequencing, Genome Analysis, Vol 1 (Davies and Tilgham, Eds.), Cold Spring Harbor Press, pp. 39-81 (1990). Maniatis, et al., Molecular Cloning, A Laboratory Manual, Cold Spring Harbor Press (1989). Nelson, et al., Nature Genetics 4: 11-18 (1993). Pirrung, et al., U.S. Pat. No. 5,143,854 (1992). Riles, et al., Genetics 134:81-150 (1993). Schena, M. et al., Proc. Nat. Acad. Sci. USA 89:3894-3898 (1992). Southern, et al., Genomics 13:1008-1017 (1992).

SUMMARY OF THE INVENTION

Methods are provided for forming a microarray of analyte-assay regions on a solid support, where each region in the array has a known amount of a selected, analyte-specific reagent. The method involves first loading a solution of a selected analyte-specific reagent in a reagent-dispensing device having an elongate capillary channel (i) formed by spaced-apart, coextensive elongate members, (ii) adapted to hold a quantity of the reagent solution and (iii) having a tip region at which aqueous solution in the channel forms a meniscus. The channel is preferably formed by a pair of spaced-apart tapered elements. The microarray compositions find use in the multiplexed detection and quantitation of ligands, e.g. antigens or antibodies, in a miniaturized format.

In another aspect, the invention includes a substrate with a surface having a microarray of at least $10^3$ distinct polynucleotide or polypeptide biopolymers in a surface area of less than about 1 $cm^2$. Each distinct biopolymer is disposed at a separate, defined position in said array, has a length of at least 50 subunits, and is present in a defined amount between about 0.1 femtomoles and 100 nanomoles.

The substrate may be used for detecting binding of ligands to a plurality of different-sequence, immobilized biopolymers. The substrate includes, in one aspect, a glass support, a coating of a polycationic polymer, such as polylysine, on said surface of the support, and an array of distinct biopolymers electrostatically bound non-covalently to said coating, where each distinct biopolymer is disposed at a separate, defined position in a surface array.

DETAILED DESCRIPTION OF THE INVENTION

Methods and compositions are provided for forming a microarray of polypeptide regions on a solid support, where each region in the array has a known amount of a selected polypeptide. A robotic printer is used to deposit microdrops of protein solutions onto a derivatized planar surface substrate, where the derivatized surface binds the polypeptide, e.g. poly-lysine, and the like. The substrate with a surface having a microarray is spotted at a high density, usually of at least $10^3$ distinct polypeptide in a surface area of less than about 1 cm$^2$. Each distinct polypeptide is present in a defined amount between about 0.1 femtomoles and 100 nanomoles. Any polypeptide can be used, although generally the polypeptide will be at least about 50 amino acids in length.

The microarrays are widely used in quantitative and analytical methods for the detection and quantitation of proteins, or compounds that interact with proteins, such as polynucleotides, hormones, vitamins and other co-factors, etc. Typically a sample comprising ligands that are suspected of binding to a polypeptide immobilized on the microarray are added to the microarray under conditions that allow specific binding between the polypeptide and the ligand. The unbound sample is washed from the microarray, and the bound ligand is detected by any suitable method, e.g. through the use of detectable labels present on the ligand, or provided in a second, detecting step. Sample consumption is much lower than traditional immunoassays due to the highly parallel and miniaturized format of the present invention. The quantitative measurement of many components in parallel allows diagnosis and recognition of physiological and phenotypic characteristics of a sample to be based on a multidimensional pattern of expression, rather than simply a few parameters.

In one embodiment of the invention, comparative fluorescence is used to monitor the presence of bound ligands to the microarray. The use of comparative fluorescence measurements allows greater precision across a wide range of ligand concentrations and binding affinities, as compared to methods that measure the absolute amount of bound ligand.

In one embodiment of the invention, the biopolymers are polypeptides, e.g. antigens, antibodies, receptors, etc., that have functional binding properties imparted by the three-dimensional structure of the polypeptide, which structure is frequently dependent on contacts made between non-contiguous amino acid residues, such as disulphide bonds between cysteine residues, hydrophobic pockets, and the like. Such binding properties include the specific binding between a protein receptor and one or more of its naturally occurring ligands, for example cytokines and cytokine receptors, hormones and hormone receptors, chemokines and chemokine receptors, etc., including a range of protein and polypeptide molecules that provide for specific interactions within a biological system. DNA binding proteins, e.g. nuclear hormone receptors; transcription factors, etc. may be provided on a microarray, where the proteins retain the ability to specifically define their cognate DNA motif. Microarrays that maintain binding properties of antigen specific immunological receptors are of particular interest, which receptors include antibodies, T cell antigen receptors, and major histocompatibility complex proteins.

These and other objects and features of the invention will become more fully apparent when the following detailed description of the invention is read in conjunction with the accompanying figures.

DEFINITIONS

Unless indicated otherwise, the terms defined below have the following meanings:

"Ligand" refers to one member of a ligand/anti-ligand binding pair. The ligand may be, for example, one of the nucleic acid strands in a complementary, hybridized nucleic acid duplex binding pair; an effector molecule in an effector/receptor binding pair; or an antigen in an antigen/antibody or antigen/antibody fragment binding pair.

"Anti-ligand" refers to the opposite member of a ligand/anti-ligand binding pair. The anti-ligand may be the other of the nucleic acid strands in a complementary, hybridized nucleic acid duplex binding pair; the receptor molecule in an effector/receptor binding pair; or an antibody or antibody fragment molecule in antigen/antibody or antigen/antibody fragment binding pair, respectively.

"Analyte" or "analyte molecule" refers to a molecule, typically a macromolecule, such as a polynucleotide or polypeptide, whose presence, amount, and/or identity are to be determined. The analyte is one member of a ligand/anti-ligand pair.

"Analyte-specific assay reagent" refers to a molecule effective to bind specifically to an analyte molecule. The reagent is the opposite member of a ligand/anti-ligand binding pair.

An "array of regions on a solid support" is a linear or two-dimensional array of preferably discrete regions, each having a finite area, formed on the surface of a solid support.

A "microarray" is an array of regions having a density of discrete regions of at least about 100/cm$^2$, and preferably at least about 1000/cm$^2$. The regions in a microarray have typical dimensions, e.g., diameters, in the range of between about 10-250 µm, and are separated from other regions in the array by about the same distance.

A support surface is "hydrophobic" if a aqueous-medium droplet applied to the surface does not spread out substantially beyond the area size of the applied droplet. That is, the surface acts to prevent spreading of the droplet applied to the surface by hydrophobic interaction with the droplet.

A "meniscus" means a concave or convex surface that forms on the bottom of a liquid in a channel as a result of the surface tension of the liquid.

"Distinct biopolymers", as applied to the biopolymers forming a microarray, means an array member which is distinct from other array members on the basis of a different biopolymer sequence, and/or different concentrations of the same or distinct biopolymers, and/or different mixtures of distinct or different-concentration biopolymers. Thus an array of "distinct polynucleotides" means an array containing, as its members, (i) distinct polynucleotides, which may have a defined amount in each member, (ii) different, graded concentrations of given-sequence polynucleotides, and/or (iii) different-composition mixtures of two or more distinct polynucleotides.

"Cell type" means a cell from a given source, e.g., a tissue, or organ, or a cell in a given state of differentiation, or a cell associated with a given pathology or genetic makeup.

Method of Microarray Formation

This section describes a method of forming a microarray of analyte-assay regions on a solid support or substrate, where each region in the array has a known amount of a selected, analyte-specific reagent.

Figure 1:
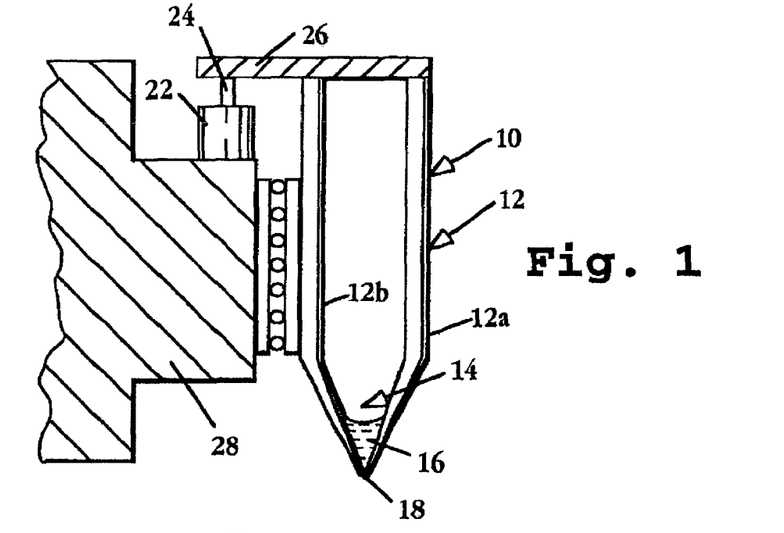
FIG. 1 is a side view of a reagent-dispensing device having a open-capillary dispensing head constructed for use in one embodiment of the invention.

FIG. 1 illustrates, in a partially schematic view, a reagent-dispensing device 10 useful in practicing the method. The device generally includes a reagent dispenser 12 having an elongate open capillary channel 14 adapted to hold a quantity of the reagent solution, such as indicated at 16, as will be described below. The capillary channel is formed by a pair of spaced-apart, coextensive, elongate members 12a, 12b which are tapered toward one another and converge at a tip or tip region 18 at the lower end of the channel. More generally, the open channel is formed by at least two elongate, spaced-apart members adapted to hold a quantity of reagent solutions and having a tip region at which aqueous solution in the channel forms a meniscus, such as the concave meniscus illustrated at 20 in FIG. 2A. The advantages of the open channel construction of the dispenser are discussed below.

With continued reference to FIG. 1, the dispenser device also includes structure for moving the dispenser rapidly toward and away from a support surface, for effecting deposition of a known amount of solution in the dispenser on a support, as will be described below with reference to FIGS. 2A-2C. In the embodiment shown, this structure includes a solenoid 22 which is activatable to draw a solenoid piston 24 rapidly downwardly, then release the piston, e.g., under spring bias, to a normal, raised position, as shown. The dispenser is carried on the piston by a connecting member 26, as shown. The just-described moving structure is also referred to herein as dispensing means for moving the dispenser into engagement with a solid support, for dispensing a known volume of fluid on the support.

The dispensing device just described is carried on an arm 28 that may be moved either linearly or in an x-y plane to position the dispenser at a selected deposition position, as will be described.

Figure 2A:
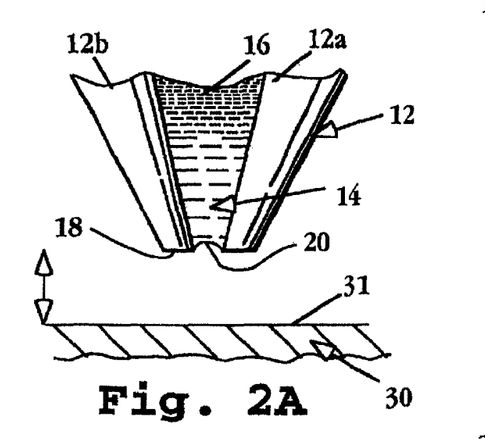
FIGS. 2A-2C illustrate steps in the delivery of a fixed-volume bead on a hydrophobic surface employing the dispensing head from FIG. 1, in accordance with one embodiment of the method of the invention.
Figure 2B:
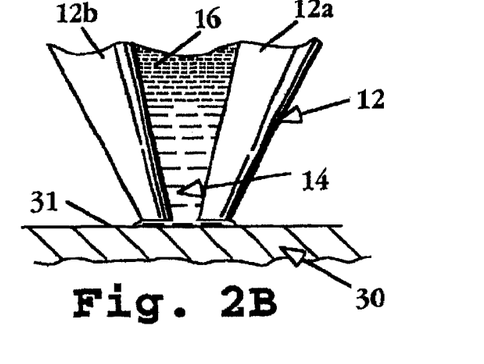
Figure 2C:
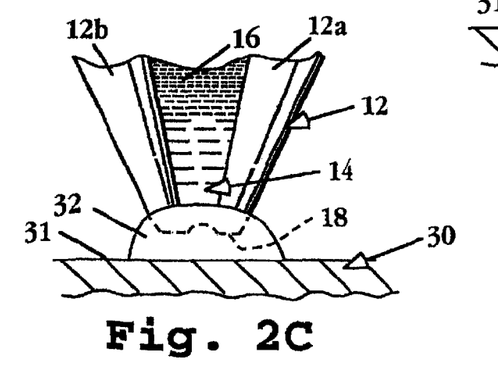

FIGS. 2A-2C illustrate the method of depositing a known amount of reagent solution in the just-described dispenser on the surface of a solid support, such as the support indicated at 30. The support is a polymer, glass, or other solid-material support having a surface indicated at 31.

In one general embodiment, the surface is a relatively hydrophilic, i.e., wettable surface, such as a surface having native, bound or covalently attached charged groups. One such surface described below is a glass surface having an absorbed layer of a polycationic polymer, such as poly-l-lysine.

In another embodiment, the surface has or is formed to have a relatively hydrophobic character, i.e., one that causes aqueous medium deposited on the surface to bead. A variety of known hydrophobic polymers, such as polystyrene, polypropylene, or polyethylene have desired hydrophobic properties, as do glass and a variety of lubricant or other hydrophobic films that may be applied to the support surface.

Initially, the dispenser is loaded with a selected analyte-specific reagent solution, such as by dipping the dispenser tip, after washing, into a solution of the reagent, and allowing filling by capillary flow into the dispenser channel. The dispenser is now moved to a selected position with respect to a support surface, placing the dispenser tip directly above the support-surface position at which the reagent is to be deposited. This movement takes place with the dispenser tip in its raised position, as seen in FIG. 2A, where the tip is typically at least several 1-5 mm above the surface of the substrate.

With the dispenser so positioned, solenoid 22 is now activated to cause the dispenser tip to move rapidly toward and away from the substrate surface, making momentary contact with the surface, in effect, tapping the tip of the dispenser against the support surface. The tapping movement of the tip against the surface acts to break the liquid meniscus in the tip channel, bringing the liquid in the tip into contact with the support surface. This, in turn, produces a flowing of the liquid into the capillary space between the tip and the surface, acting to draw liquid out of the dispenser channel, as seen in FIG. 2B.

FIG. 2C shows flow of fluid from the tip onto the support surface, which in this case is a hydrophobic surface. The figure illustrates that liquid continues to flow from the dispenser onto the support surface until it forms a liquid bead 32. At a given bead size, i.e., volume, the tendency of liquid to flow onto the surface will be balanced by the hydrophobic surface interaction of the bead with the support surface, which acts to limit the total bead area on the surface, and by the surface tension of the droplet, which tends toward a given bead curvature. At this point, a given bead volume will have formed, and continued contact of the dispenser tip with the bead, as the dispenser tip is being withdrawn, will have little or no effect on bead volume.

For liquid-dispensing on a more hydrophilic surface, the liquid will have less of a tendency to bead, and the dispensed volume will be more sensitive to the total dwell time of the dispenser tip in the immediate vicinity of the support surface, e.g., the positions illustrated in FIGS. 2B and 2C.

The desired deposition volume, i.e., bead volume, formed by this method is preferably in the range 2 pl (picoliters) to 2 nl (nanoliters), although volumes as high as 100 nl or more may be dispensed. It will be appreciated that the selected dispensed volume will depend on (i) the "footprint" of the dispenser tip, i.e., the size of the area spanned by the tip, (ii) the hydrophobicity of the support surface, and (iii) the time of contact with and rate of withdrawal of the tip from the support surface. In addition, bead size may be reduced by increasing the viscosity of the medium, effectively reducing the flow time of liquid from the dispenser onto the support surface. The drop size may be further constrained by depositing the drop in a hydrophilic region surrounded by a hydrophobic grid pattern on the support surface.

In a typical embodiment, the dispenser tip is tapped rapidly against the support surface, with a total residence time in contact with the support of less than about 1 msec, and a rate of upward travel from the surface of about 10 cm/sec.

Assuming that the bead that forms on contact with the surface is a hemispherical bead, with a diameter approximately equal to the width of the dispenser tip, as shown in FIG. 2C, the volume of the bead formed in relation to dispenser tip width (d) is given in Table 1 below. As seen, the volume of the bead ranges between 2 pl to 2 nl as the width size is increased from about 20 to 200 μm.

TABLE 1

| d | Volume (nl) |
|---|---|
| 20 μm | $2 \times 10^{-3}$ |
| 50 μm | $3.1 \times 10^{-2}$ |
| 100 μm | $2.5 \times 10^{-1}$ |
| 200μ | 2 |

At a given tip size, bead volume can be reduced in a controlled fashion by increasing surface hydrophobicity, reducing time of contact of the tip with the surface, increasing rate of movement of the tip away from the surface, and/or increasing the viscosity of the medium. Once these parameters are fixed, a selected deposition volume in the desired pl to nl range can be achieved in a repeatable fashion.

After depositing a bead at one selected location on a support, the tip is typically moved to a corresponding position on a second support, a droplet is deposited at that position, and this process is repeated until a liquid droplet of the reagent has been deposited at a selected position on each of a plurality of supports.

The tip is then washed to remove the reagent liquid, filled with another reagent liquid and this reagent is now deposited at each another array position on each of the supports. In one embodiment, the tip is washed and refilled by the steps of (i) dipping the capillary channel of the device in a wash solution, (ii) removing wash solution drawn into the capillary channel, and (iii) dipping the capillary channel into the new reagent solution.

From the foregoing, it will be appreciated that the tweezers-like, open-capillary dispenser tip provides the advantages that (i) the open channel of the tip facilitates rapid, efficient washing and drying before reloading the tip with a new reagent, (ii) passive capillary action can load the sample directly from a standard microwell plate while retaining sufficient sample in the open capillary reservoir for the printing of numerous arrays, (iii) open capillaries are less prone to clogging than closed capillaries, and (iv) open capillaries do not require a perfectly faced bottom surface for fluid delivery.

Figure 3:
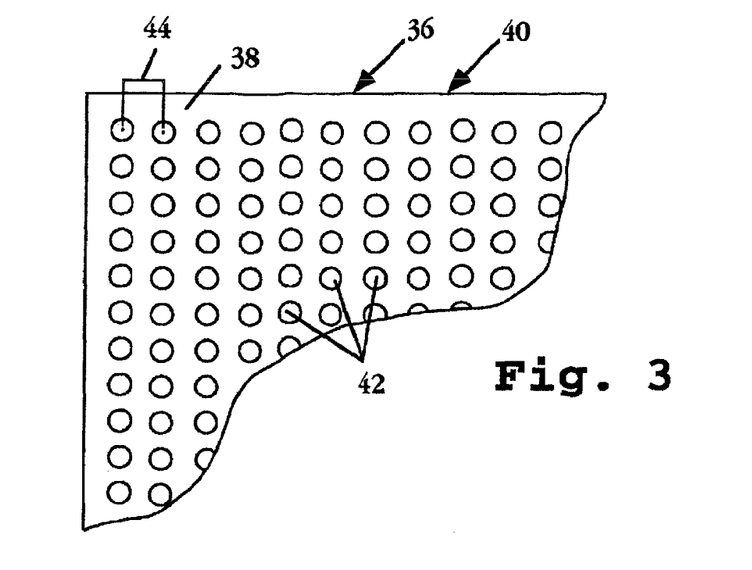
FIG. 3 shows a portion of a two-dimensional array of analyte-assay regions constructed according to the method of the invention.

A portion of a microarray 36 formed on the surface 38 of a solid support 40 in accordance with the method just described is shown in FIG. 3. The array is formed of a plurality of analyte-specific reagent regions, such as regions 42, where each region may include a different analyte-specific reagent. As indicated above, the diameter of each region is preferably between about 20-200 μm. The spacing between each region and its closest (non-diagonal) neighbor, measured from center-to-center (indicated at 44), is preferably in the range of about 20-400 μm. Thus, for example, an array having a center-to-center spacing of about 250 μm contains about 40 regions/cm or 1,600 regions/cm². After formation of the array, the support is treated to evaporate the liquid of the droplet forming each region, to leave a desired array of dried, relatively flat regions. This drying may be done by heating or under vacuum.

In some cases, it is desired to first rehydrate the droplets containing the analyte reagents to allow for more time for adsorption to the solid support. It is also possible to spot out the analyte reagents in a humid environment so that droplets do not dry until the arraying operation is complete.

Automated Apparatus for Forming Arrays

In another aspect, the invention includes an automated apparatus for forming an array of analyte-assay regions on a solid support, where each region in the array has a known amount of a selected, analyte-specific reagent.

Figure 4:
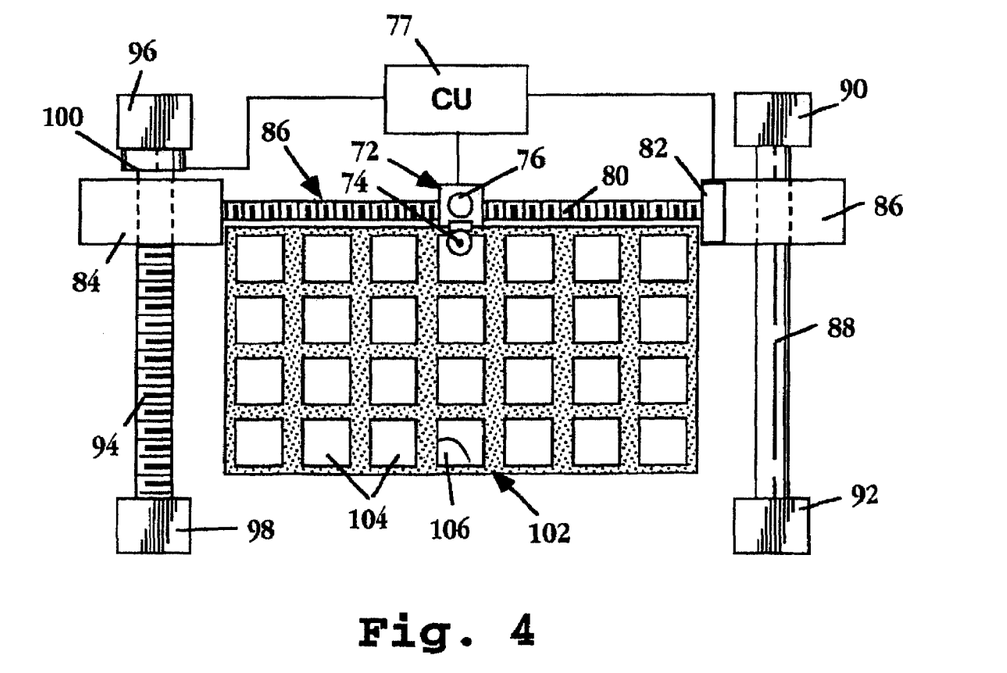
FIG. 4 is a planar view showing components of an automated apparatus for forming arrays in accordance with the invention.

The apparatus is shown in planar, and partially schematic view in FIG. 4. A dispenser device 72 in the apparatus has the basic construction described above with respect to FIG. 1, and includes a dispenser 74 having an open-capillary channel terminating at a tip, substantially as shown in FIGS. 1 and 2A-2C.

The dispenser is mounted in the device for movement toward and away from a dispensing position at which the tip of the dispenser taps a support surface, to dispense a selected volume of reagent solution, as described above. This movement is effected by a solenoid 76 as described above. Solenoid 76 is under the control of a control unit 77 whose operation will be described below. The solenoid is also referred to herein as dispensing means for moving the device into tapping engagement with a support, when the device is positioned at a defined array position with respect to that support.

The dispenser device is carried on an arm 74 which is threadedly mounted on a worm screw 80 driven (rotated) in a desired direction by a stepper motor 82 also under the control of unit 77. At its left end in the figure screw 80 is carried in a sleeve 84 for rotation about the screw axis. At its other end, the screw is mounted to the drive shaft of the stepper motor, which in turn is carried on a sleeve 86. The dispenser device, worm screw, the two sleeves mounting the worm screw, and the stepper motor used in moving the device in the "x" (horizontal) direction in the figure form what is referred to here collectively as a displacement assembly 86.

The displacement assembly is constructed to produce precise, micro-range movement in the direction of the screw, i.e., along an x axis in the figure. In one mode, the assembly functions to move the dispenser in x-axis increments having a selected distance in the range 5-25 μm. In another mode, the dispenser unit may be moved in precise x-axis increments of several microns or more, for positioning the dispenser at associated positions on adjacent supports, as will be described below.

The displacement assembly, in turn, is mounted for movement in the "y" (vertical) axis of the figure, for positioning the dispenser at a selected y axis position. The structure mounting the assembly includes a fixed rod 88 mounted rigidly between a pair of frame bars 90, 92, and a worm screw 94 mounted for rotation between a pair of frame bars 96, 98. The worm screw is driven (rotated) by a stepper motor 100 which operates under the control of unit 77. The motor is mounted on bar 96, as shown.

The structure just described, including worm screw 94 and motor 100, is constructed to produce precise, micro-range movement in the direction of the screw, i.e., along a y axis in the figure. As above, the structure functions in one mode to move the dispenser in y-axis increments having a selected distance in the range 5-250 μm, and in a second mode, to move the dispenser in precise y-axis increments of several microns (μm) or more, for positioning the dispenser at associated positions on adjacent supports.

The displacement assembly and structure for moving this assembly in the y axis are referred to herein collectively as positioning means for positioning the dispensing device at a selected array position with respect to a support.

A holder 102 in the apparatus functions to hold a plurality of supports, such as supports 104 on which the microarrays of reagent regions are to be formed by the apparatus. The holder provides a number of recessed slots, such as slot 106, which receive the supports, and position them at precise selected positions with respect to the frame bars on which the dispenser moving means is mounted.

As noted above, the control unit in the device functions to actuate the two stepper motors and dispenser solenoid in a sequence designed for automated operation of the apparatus in forming a selected microarray of reagent regions on each of a plurality of supports.

The control unit is constructed, according to conventional microprocessor control principles, to provide appropriate signals to each of the solenoid and each of the stepper motors, in a given timed sequence and for appropriate signaling time. The construction of the unit, and the settings that are selected by the user to achieve a desired array pattern, will be understood from the following description of a typical apparatus operation.

Initially, one or more supports are placed in one or more slots in the holder. The dispenser is then moved to a position directly above a well (not shown) containing a solution of the first reagent to be dispensed on the support(s). The dispenser solenoid is actuated now to lower the dispenser tip into this well, causing the capillary channel in the dispenser to fill. Motors 82, 100 are now actuated to position the dispenser at a selected array position at the first of the supports. Solenoid actuation of the dispenser is then effective to dispense a selected-volume droplet of that reagent at this location. As noted above, this operation is effective to dispense a selected volume preferably between 2 µl and 2 nl of the reagent solution.

The dispenser is now moved to the corresponding position at an adjacent support and a similar volume of the solution is dispensed at this position. The process is repeated until the reagent has been dispensed at this preselected corresponding position on each of the supports.

Where it is desired to dispense a single reagent at more than two array positions on a support, the dispenser may be moved to different array positions at each support, before moving the dispenser to a new support, or solution can be dispensed at individual positions on each support, at one selected position, then the cycle repeated for each new array position.

To dispense the next reagent, the dispenser is positioned over a wash solution (not shown), and the dispenser tip is dipped in and out of this solution until the reagent solution has been substantially washed from the tip. Solution can be removed from the tip, after each dipping, by vacuum, compressed air spray, sponge, or the like.

The dispenser tip is now dipped in a second reagent well, and the filled tip is moved to a second selected array position in the first support. The process of dispensing reagent at each of the corresponding second-array positions is then carried out as above. This process is repeated until an entire microarray of reagent solutions on each of the supports has been formed.

Microarray Substrate

This section describes embodiments of a substrate having a microarray of biological polymers carried on the substrate surface, in particular a microarray of distinct polypeptides bound on a glass slide coated with a polycationic polymer is described.

A substrate is formed according to another aspect of the invention, and intended for use in detecting binding of labeled ligands to one or more of a plurality distinct biopolymers. In one embodiment, the substrate includes a glass substrate having formed on its surface, a coating of a polycationic polymer, preferably a cationic polypeptide, such as poly-lysine or poly-arginine. Formed on the polycationic coating is a microarray of distinct biopolymers, each localized at known selected array regions, such as regions.

The slide may be coated by placing a uniform-thickness film of a polycationic polymer, e.g., poly-l-lysine, on the surface of a slide and drying the film to form a dried coating. The amount of polycationic polymer added is sufficient to form at least a monolayer of polymers on the glass surface. The polymer film is bound to surface via electrostatic binding between negative silyl-OH groups on the surface and charged amine groups in the polymers. Poly-l-lysine coated glass slides may be obtained commercially, e.g., from Sigma Chemical Co. (St. Louis, Mo.).

A suitable microarray substrate is also made through chemical derivatization of glass. Silane compounds with appropriate leaving groups on a terminal Si will covalently bond to glass surfaces. A derivatization molecule can be designed to confer the desired chemistry to the surface of the glass substrate. An example of such a bifunctional reagent is amino-propyl-tri(ethoxy)silane, which reacts with glass surfaces at the tri(ethoxy)silane portion of the molecule while leaving the amino portion of the molecule free. Surfaces having terminal amino groups are suitable for adsorption of biopolymers in the same manner as poly-lysine coated slides. The identity of the terminal surface group can be modified by further chemical reaction. For example, reaction of the terminal amine in the above example with glutaraldehyde results in a terminal aldehyde group. Further layers of modification may be applied to achieve the desired reactivity before spotting the microarray, such as by application of a Protein A or Protein G solution to the silynated glass. Additional surfaces that bind polypeptides are nitrocellulose-coated glass slides, available commercially from Schleicher and Schuell, and protein-binding plastics such as polystyrene.

The spotted polypeptides may be attached by either adsorption or covalent bonding. Adsorption occurs through electrostatic, hydrophobic, Van der Waals, or hydrogen-bonding interactions between the spotted polypeptide and the array substrate. Simple application of the polypeptide solution to the surface in an aqueous environment is sufficient to adsorb the polypeptide. Covalent attachment is achieved by reaction of functional groups on the polypeptide with a chemically activated surface. For example, if the surface has been activated with a highly reactive electrophilic group such as an aldehyde or succinimide group, unmodified polypeptides react at amine groups, as at lysine residues or the terminal amine, to form a covalent bond.

To form the microarray, defined volumes of distinct biopolymers are deposited on the polymer-coated slide, as described in Section II. According to an important feature of the substrate, the deposited biopolymers remain bound to the coated slide surface non-covalently when an aqueous sample is applied to the substrate under conditions that allow binding of labeled ligands in the sample to cognate binding partners in the substrate array.

In a preferred embodiment, each microarray contains at least $10^3$ distinct polynucleotide or polypeptide biopolymers per surface area of less than about 1 $cm^2$. In one embodiment, the microarray contains 400 regions in an area of about 16 $mm^2$, or $2.5 \times 10^3$ regions/$cm^2$. Also in a preferred embodiment, the biopolymers in each microarray region are present in a defined amount between about 0.1 femtomoles and 100 nanomoles (in the case of polynucleotides). As above, the ability to form high-density arrays of this type, where each region is formed of a well-defined amount of deposited material, can be achieved in accordance with the microarray-forming method described in Section II.

Also in a preferred embodiment, the biopolymers have lengths of at least about 50 units, e.g. amino acids, nucleotides, etc., i.e., substantially longer than polymers which can be formed in high-density arrays by various in situ synthesis schemes.

The polypeptide biopolymers may comprise polypeptides from any source. Polypeptides of interest include those isolated from cells or other biological sources, synthesized polypeptides, including synthesized peptides and peptides selected from combinatorial libraries, polypeptides synthesized from recombinant nucleic acids, and the like. In one embodiment, the polypeptides are isolated from phage display libraries or clones (see Huse et al. (1989) Science. 1989 246(4935):1275-81; Winter et al. (1994) Annu Rev Immunol. 12:433-55; Clackson et al. (1991) Nature 352(6336):624-8). Usually the polypeptides on each discrete region of the array will be substantially pure.

Uses of the Microarrays

Arrays of whole cells, peptides, enzymes, antibodies, antigens, receptors, ligands, phospholipids, polymers, drug congener preparations or chemical substances can be fabricated by the means described in this invention for large scale screening assays in medical diagnostics, drug discovery, molecular biology, immunology and toxicology.

Microarrays of immobilized polypeptides prepared in accordance with the invention can be used for large scale binding assays in numerous diagnostic and screening applications. The multiplexed measurement of quantitative variation in levels of large numbers of proteins allows the recognition of patterns defined by several to many different proteins. One can simultaneously assess many physiological parameters and disease-specific patterns.

One embodiment of the invention involves the separation, identification and characterization of proteins present in a biological sample. For example, by comparison of disease and control samples, it is possible to identify "disease specific proteins". These proteins may be used as targets for drug development or as molecular markers of disease.

Polypeptide arrays are used to monitor the expression levels of proteins in a sample where such samples may include biopsy of a tissue of interest, cultured cells, microbial cell populations, biological fluids, including blood, plasma, lymph, synovial fluid, cerebrospinal fluid, cell lysates, culture supernatants, amniotic fluid, etc., and derivatives thereof. Of particular interest are clinical samples of biological fluids, including blood and derivatives thereof, cerebrospinal fluid, urine, saliva, lymph, synovial fluids, etc. Such measurements may be quantitative, semi-quantitative, or qualitative. Where the assay is to be quantitative or semi-quantitative, it will preferably comprise a competition-type format, for example between labeled and unlabeled samples, or between samples that are differentially labeled.

Assays to detect the presence of ligands to the immobilized polypeptides may be performed as follows, although the methods need not be limited to those set forth herein.

Samples, fractions or aliquots thereof are added to a microarray comprising bound polypeptide. Samples may comprise a wide variety of biological fluids or extracts as described above. Preferably, a series of standards, containing known concentrations of control ligand(s) is assayed in parallel with the samples or aliquots thereof to serve as controls.

The incubation time should be sufficient for ligand molecules to bind the polypeptides. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

In order to detect the presence of bound ligands, a variety of methods may be used. These fall into three general groups. The ligand itself may be labeled with a detectable label, and the amount of bound label directly measured. Alternatively, the labeled sample may be mixed with a differentially labeled, or unlabeled sample in a competition assay. In yet another embodiment, the sample itself is not labeled, but a second stage labeled reagent is added in order to quantitate the amount of ligand present.

Examples of labels that permit direct measurement of ligand binding include radiolabels, such as $^3$H or $^{125}$I, fluorescers, dyes, beads, chemilumninescers, colloidal particles, and the like. Suitable fluorescent dyes are known in the art, including fluorescein isothiocyanate (FITC); rhodamine and rhodamine derivatives; Texas Red; phycoerythrin; allophycocyanin; 6-carboxyfluorescein (6-FAM); 2',7'-dimethoxy-4', 5'-dichloro-6-carboxyfluorescein (JOE); 6-carboxy-X-rhodamine (ROX); 6-carboxy-2',4',7',4,7-hexachlorofluorescein (HEX); 5-carboxyfluorescein (5-FAM); N,N,N',N'-tetramethyl-6-carboxyrhodamine (TAMRA); sulfonated rhodamine; Cy3; Cy5; etc. Preferably the compound to be labeled is combined with an activated dye that reacts with a group present on the ligand, e.g. amine groups, thiol groups, aldehyde groups, etc.

Particularly where a second stage detection is performed, for example by the addition of labeled antibodies that recognize the ligand, the label can be a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The second stage binding reagent may be any compound that binds the ligands with sufficient specificity such that it can be distinguished from other components present. In a preferred embodiment, second stage binding reagents are antibodies specific for the ligand, either monoclonal or polyclonal sera, e.g. mouse anti-human antibodies, etc.

For an amplification of signal, the ligand may be labeled with an agent such as biotin, digoxigenin, etc., where the second stage reagent will comprise avidin, streptavidin, anti-digoxigenin antibodies, etc. as appropriate for the label.

Microarrays can be scanned to detect binding of the ligands, e.g. by using a scanning laser microscope, by fluorimetry, a modified ELISA plate reader, etc. For example, a scanning laser microscope may perform a separate scan, using the appropriate excitation line, for each of the fluorophores used. The digital images generated from the scan are then combined for subsequent analysis. For any particular array element, the ratio of the fluorescent signal with one label is compared to the fluorescent signal from the other label DNA, and the relative abundance determined.

The microarrays and methods of detecting ligands may be used for a number of screening, investigative and diagnostic assays. In one application, an array of antibodies is bound to total protein from an organism to monitor protein expression for research or diagnostic purposes. Labeling total protein from a normal cell with one color fluorophore and total protein from a diseased cell with another color fluorophore and simultaneously binding the two samples to the same array allows for differential protein expression to be measured as the ratio of the two fluorophore intensities. This two-color experiment can be used to monitor expression in different tissue types, disease states, response to drugs, or response to environmental factors.

In screening assays, for example to determine whether a protein or proteins are implicated in a disease pathway or are correlated with a disease-specific phenotype, measurements may be made from cultured cells. Such cells may be experimentally manipulated by the addition of pharmacologically active agents that act on a target or pathway of interest. This application is important for elucidation of biological function or discovery of therapeutic targets.

For many diagnostic and investigative purposes it is useful to measurement levels of ligands, e.g. protein ligands, in blood or serum. This application is important for the discovery and diagnosis of clinically useful markers that correlate with a particular diagnosis or prognosis. For example, by monitoring a range of antibody or T cell receptor specificities in parallel, one may determine the levels and kinetics of antibodies during the course of autoimmune disease, during infection, through graft rejection, etc. Alternatively, novel protein markers associated with a disease of interest may be developed through comparisons of normal and diseased blood sample, or by comparing clinical samples at different stages of disease.

In another embodiment of the invention, the polypeptide arrays are used to detect post-translational modifications in proteins, which is important in studying signaling pathways and cellular regulation. Post-translational modifications can be detected using antibodies specific for a particular state of a protein, such as phosphorylated, glycosylated, farnesylated, etc.

The detection of these interactions between ligands and polypeptides can lead to a medical diagnosis. For example, the identity of a pathogenic microorganism can be established unambiguously by binding a sample of the unknown pathogen to an array containing many types of antibodies specific for known pathogenic antigens.

EXPERIMENTAL

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Antibody and Antigen Microarrays

A set of antibody and antigen pairs with which highly controlled experiments could be performed was assembled, using 115 different ligand/anti-ligand pairs.

Methods

Array preparation: Antibody solutions were prepared at 100-200 µg/mL in a PBS/0.02% sodium azide buffer without glycerol. The antibodies were spotted onto glass slides treated with poly-1-lysine. The slides are derivatized by the following procedure. Place slides in slide racks, then racks in chambers. Prepare cleaning solution by dissolving 70 g NaOH in 280 mL ddH2O, then adding 420 mL 95% ethanol. Total volume is 700 mL (=2×350 mL); stir until completely mixed. Pour solution into chambers with slides; cover chambers with glass lids. Mix on orbital shaker for 2 hr. Quickly transfer racks to fresh chambers filled with ddH2O. Rinse vigorously by plunging racks up and down. Repeat rinses 4× with fresh ddH2O each time. Prepare polylysine solution: 70 mL poly-L-lysine+70 mL tissue culture PBS in 560 mL water. Transfer slides to polylysine solution and shake 15 min.-1 hr. Transfer rack to fresh chambers filled with ddH2O. Plunge up and down 5× to rinse. Centrifuge slides on microtiter plate carriers for 5 min. @ 500 rpm. Dry slide racks in 45° C. vacuum oven for 10 min.

The antibodies and antigens were prepared in a 384-well microtitre plate containing at least three wells each of 110 different antibodies or antigens. A 16-tip print head on the arrayer spotted the plate three times for a total of 1152 spots, with 9-12 duplicate spots per antibody or antigen. The spacing between spots was 375 micrometers. The arrays were sealed in an airtight container. They can be stored at 4° C. for short term storage (~1 month) or frozen for longer storage.

The back sides of the slides were marked with a diamond scribe or indelible marker to delineate the location of the spots. To remove unbound protein, the arrays were dunked several times in PBS/3% non-fat milk/0.1% Tween-20, and transferred immediately to a solution of PBS/3% non-fat milk, and let block overnight at 4° C. The milk solution was first centrifuged (10 minutes at 10000×g) to remove particulate matter.

After blocking, the slides were dunked and thoroughly agitated for one minute each in three consecutive room temperature washes of 0.2×PBS to remove the unbound milk protein. The arrays remained in the last wash until application of the protein mixture.

Sample preparation: Protein solutions were prepared in a 0.1 carbonate or phosphate buffer at pH 8.0, using up to ~15 µg protein per array (when using 25 µL per array) at a concentration such that after mixing with the dye solution (see below), the final protein concentration is 0.2-2 mg/mL.

NHS-ester activated Cy-dyes (Amersham, catalog #PA23001 (Cy3) and PA25001 (Cy5)) were dissolved in a 0.1 M pH 8.0 carbonate buffer so that the final concentration of the dye after mixing with the protein solution was 100-300 µM. (Each vial of dye contains 200 nmols.) The dye and protein solutions were mixed, and allowed to react in the dark at room temperature for 45 minutes. The reference protein solution was mixed with the Cy3 dye solution, and the test protein solution with the Cy5 dye solution. The reactions were quenched by adding enough 1 M pH 8 tris or glycine to each so that at least a 200-fold excess of quencher:dye concentration was achieved.

Each mix was loaded into a microconcentrator having the appropriate molecular weight cutoff. A 3000 D cutoff captures most proteins while still removing the dye. If smaller proteins are not important, the 10000 D cutoff is faster. The mix was centrifuged according to the microconcentrator instructions. The 10000 D microcon typically requires 20 minutes and the 3000 D microcon requires 80 minutes of centrifugation at 10000×g and room temperature. After centrifuging, 3% milk blocker was added to either the Cy5 or Cy3-labeled protein mixes. (The milk must first be centrifuged to remove particulate matter: 10 minutes at 10000×g.) Add 25 μL milk for each array to be generated from the protein mix. PBS was added to each microcon to a 500 μL volume, and centrifuged again. The concentrated samples were collected into a small volume (~5 μL) of PBS to prevent drying and precipitation.

The Cy3-labeled reference protein solution was distributed to the appropriate Cy5-labeled test protein solutions, and PBS added to each mix to achieve a volume of 25 μL per array. Particulate matter or precipitate was removed by 1) filtering with a 0.45 μm spin filter, or 2) centrifuging 10 minutes at 14000×g and pipetting out the supernatant.

Detection: Each array was removed individually from the PBS wash. Without allowing the array to dry, 25 μL of the dye-labeled protein solution was placed over the spots (within the marked boundaries), with a cover slip placed over the protein solution. The cover slip has dimensions at least ¼ inch longer than the dimensions of the array. The arrays were placed in a sealed humidification chamber with a layer of PBS under the arrays, and incubated at 4° C. for approximately two hours. Each array was briefly dunked in PBS to remove the protein solution and the cover slip, and transferred immediately to a slide rack in a PBS/0.1% Tween-20 solution. After all the arrays have been racked in the PBS/Tween solution, they were washed on an orbital shaker for ~20 minutes at room temperature. The arrays were transferred to a new rack (to minimize Tween carryover) in a PBS solution and rocked gently for 5-10 minutes, then transferred to wash solutions of PBS, $H_2O$, and $H_2O$ for five minutes each of gentle agitation. The arrays were then spin-dried and scanned.

Analysis: The fluorescence intensity at each spot reflects the level of binding to that particular protein. The relative concentration between proteins in differentially dye-labeled pools is determined by comparing the fluorescence intensities between the color channels at each spot. The following method is used to determine relative concentrations.

The location of each analyte spot on the array is outlined using "gridding" software, such as GenePix or ScanAlyze, which places a boundary around each spot on the array.

The fluorescence signal from each spot is determined as the average or median of the pixel intensities within the boundary outlined using the gridding software. Each color channel is treated independently. Optionally statistical methods are used to reject "outlier" pixels within the circle, i.e. pixels that have intensities significantly outside the average pixel intensity.

The background is subtracted from the signal. The background may be determined as 1) the median or average of pixel intensities from the local area around each spot, or as 2) the median or average or pixel intensities from within certain spots or areas determined to be non-binding background areas. Statistical methods may be used to reject outlier pixels in the background.

The relative binding at each spot between proteins in the separately labeled pools is equivalent to the ratio of fluorescence intensities in the two color channels. In order for the ratio to reflect the true relative concentrations, the background-subtracted signal from one of the color channels must be multiplied by a normalization factor. The normalization factor may be determined by selecting spots for which the true concentrations are known and calculating the factor that most accurately returns the true color ratio. Alternatively, if no control spots are used, one may assume that the average binding across every spot on the array is roughly equal for the two protein pools. A normalization factor is then calculated that gives an average color ratio of one for all the spots on the array.

Once all arrays have been normalized and color ratios have calculated, changes in protein concentration from array to array may be compared. Interpretation is simplest if the same reference pool is used for each experiment.

Results:

To test the specificity, quantitation, and limits of detection of the protein array, six mixes of antigens were made in which the concentration of each protein varied uniquely across the mixes. For example, one protein changed from high to low concentration, another from low to high, and another from low to high to low. The concentrations varied three orders of magnitude over the whole set. This set of six mixes was detected at various concentrations and in various levels of fetal calf serum (FCS) background. The ability to reconstruct the actual concentration changes from the data indicated the level of performance of the microarrays.

Figure 5:
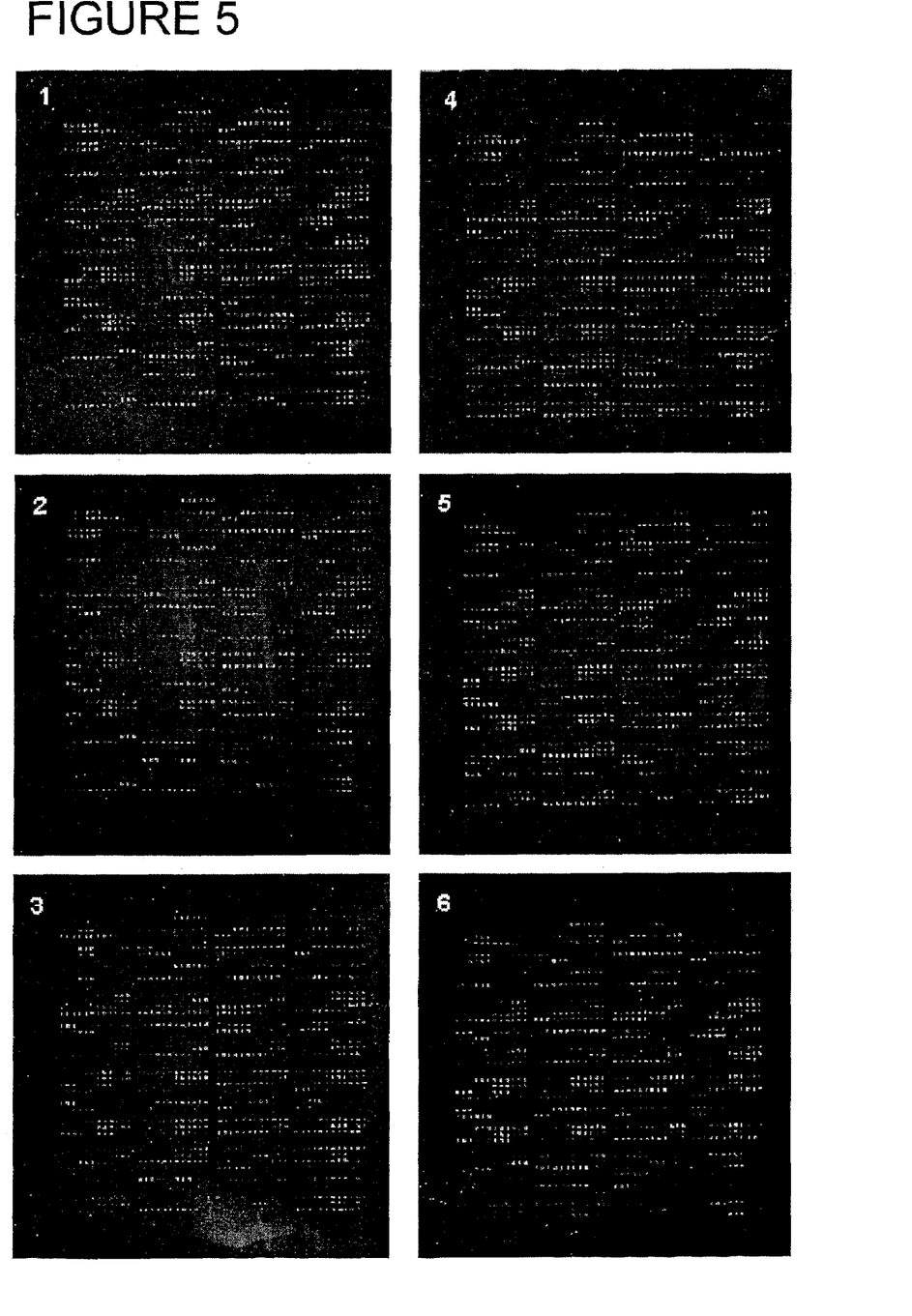
FIG. 5 shows the concentration profiles in a microarray of 110 antigens.
Figure 6:
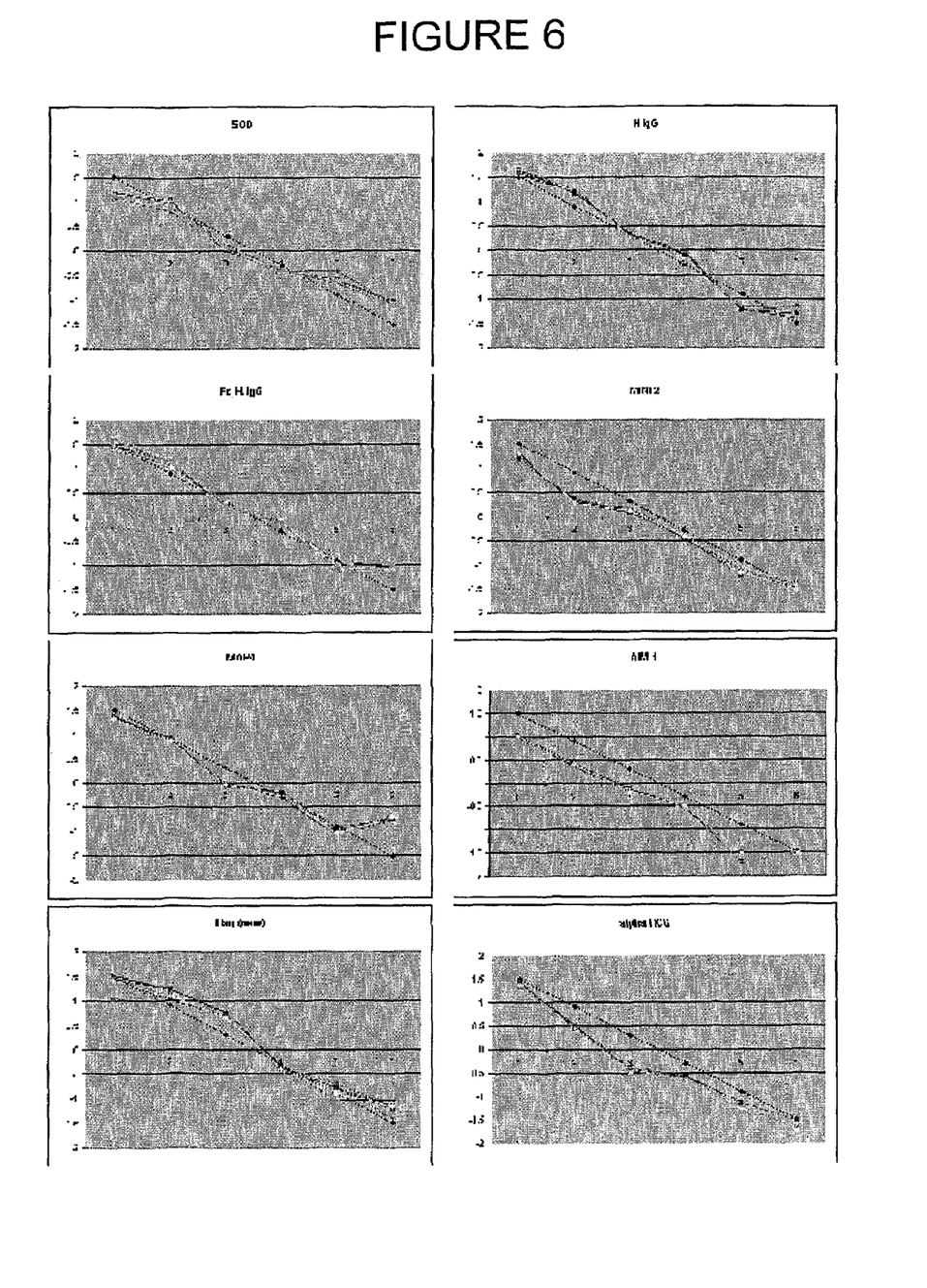
FIG. 6 shows the detection of protein as a ratio of the signal from two fluorochromes, against the dilution of the protein sample.

Microarrays were constructed containing 6 to 9 duplicate spots from each antibody. FIG. 5 presents a series of these arrays generated from the set of six unique protein mixes (labeled with the red-fluorescing dye Cy5) compared against a reference mix (labeled with the green-fluorescing dye Cy3) containing an equal amount of each protein. For each spot on the array, the red/green ratio was calculated and then plotted as a function of dilution. FIG. 6 presents plots of the log of the red-to-green ratio (R/G) versus dilution for eight of the antigens. The ideal slope, calculated as the log of the concentration ratio of the proteins, is shown as a straight solid line decreasing from 1.5 to −1.5. The other lines on the graph represent duplicate spots on the array. The slopes of the experimental data are very similar to the ideal slope over the six concentrations tested, indicating that these antibodies detected the cognate antigens specifically and quantitatively. Deviations from ideal slope appear to occur systematically between the duplicate spots, suggesting that the largest error in quantitation occurred in pipetting or data reduction rather than in random variability in the system.

Figure 7:
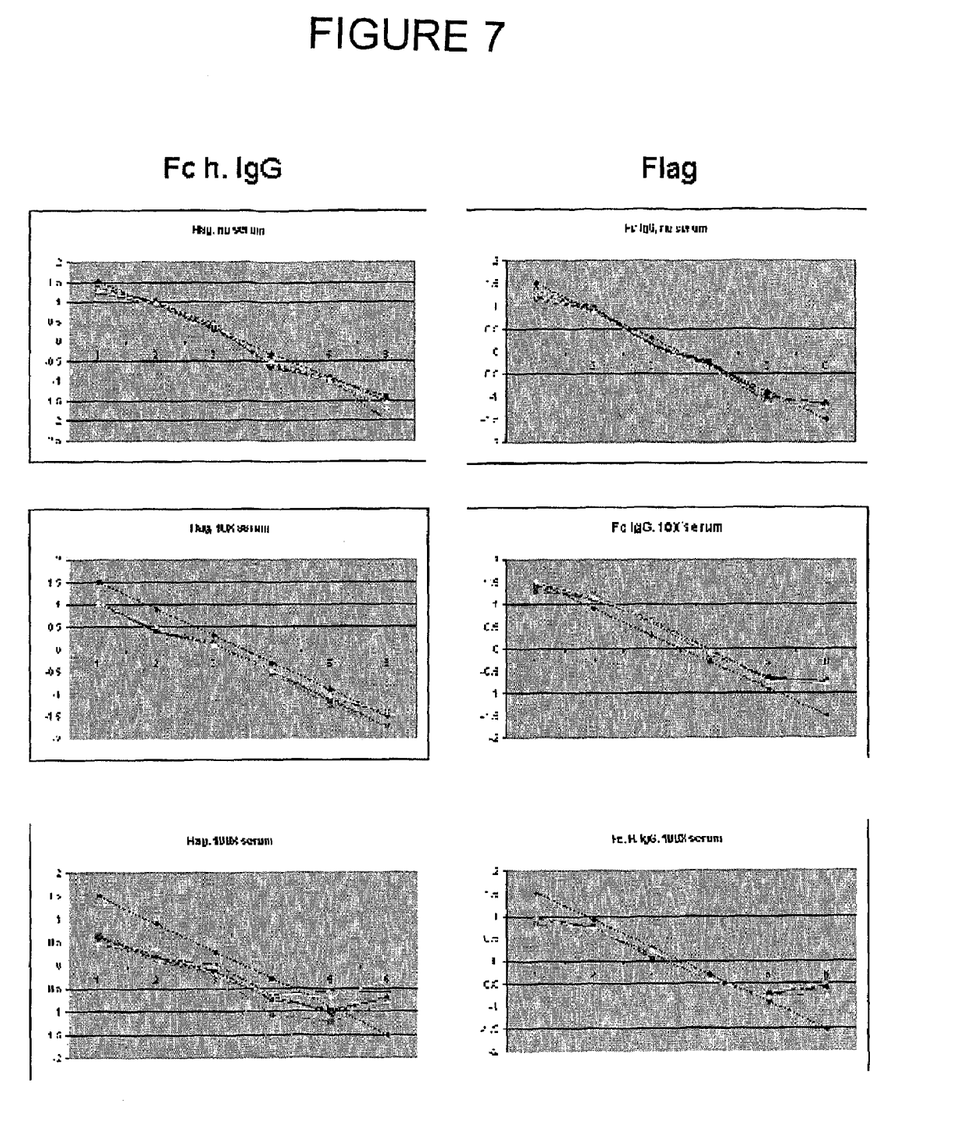
FIG. 7 shows graphs of the protein quantitation after dilution into serum.
Figure 8:
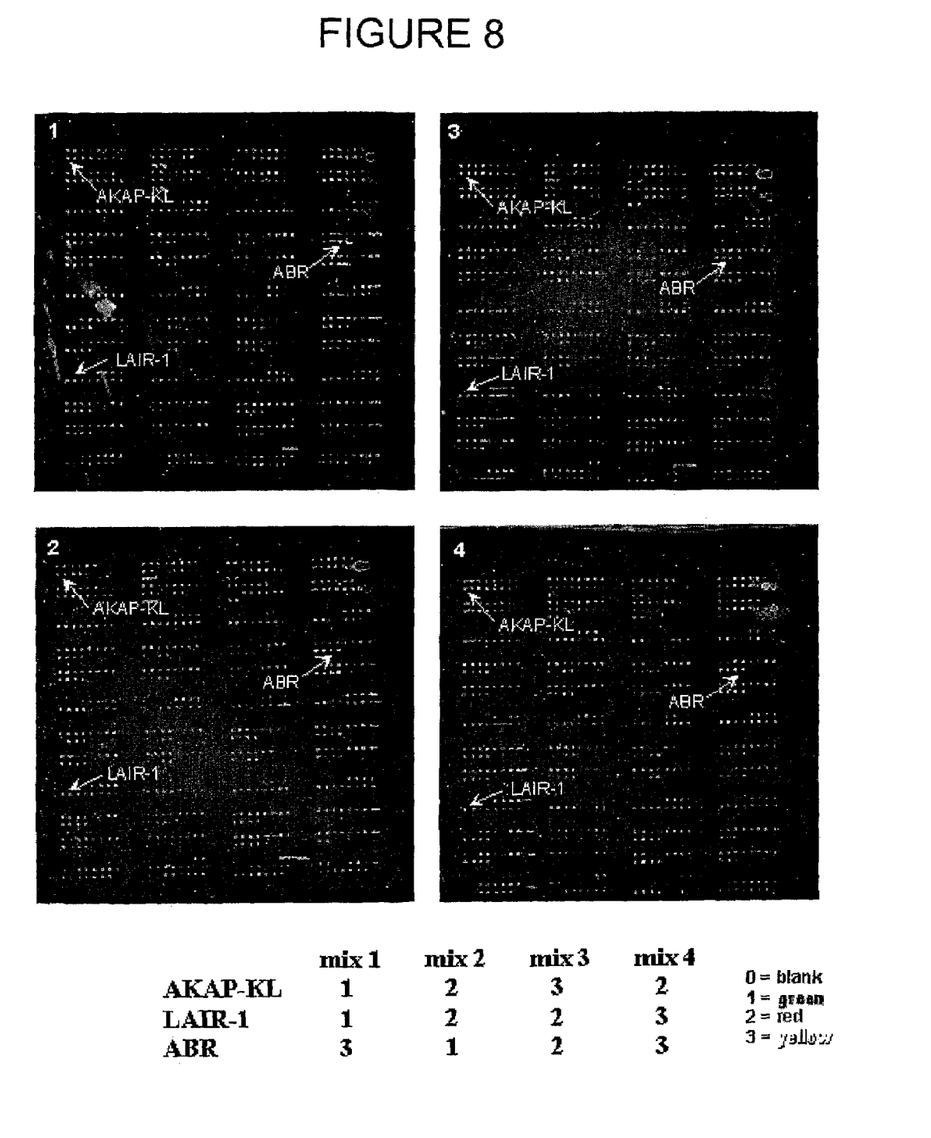
FIG. 8 depicts the combinatorial detection of multiple antibodies.

The detection of a specific protein is limited not only by concentration, but also by the concentration of background proteins. To determine how well specific proteins can be detected in high protein background, the set of unique protein mixes was spiked into varying amounts of FCS before dye labeling. FCS concentrations 10 times greater and 100 times greater than the antigen mix concentration were used. FIG. 7 shows the effect of protein background on quantitation for the proteins IgG and flag. Without the serum background, accurate quantitation is observed for both proteins over the entire concentration range, which was from 120 ng/mL to 120 pg/mL. At the 10× serum concentration, the flag protein still shows accurate quantitation, but IgG shows slight deviation from the ideal slope at the high and low limits. At the 100× serum concentration, both proteins exhibit marked deviations from the ideal slope. The partial concentrations (the antigen concentration divided by the total protein concentration) ranged from $4\times10^{-5}$ to $4\times10^{-8}$ for the 100× serum trial. Thus the partial concentration detection limit is ~$2\times10^{-6}$ for flag and ~$2\times10^{-7}$ for IgG using these antibodies. These partial concentrations are in a physiological range for many clinically interesting blood serum proteins. The results of this type of analysis for each antigen tested are presented in the table below. Antibodies were classified according to the presence of accurate quantitation over the entire range for all of the low background trial and at least part of the higher background trials (++). They were classified as (+) if they showed accurate quantitation for most of the low background trial. Many of the antibodies showed either no signal or non-specific signal.

In a second mode of detection, antigens were spotted onto the array to detect labeled antibodies. FIG. 7 presents an example of specific detection of antibodies in four unique mixes. A combinatorial labeling scheme was employed that enabled identification of specific antigen/antibody binding. An analysis similar to that described above was carried out to classify the binding specificity of antigens on the microarray. The results of that analysis are presented in the table below along with the antibody array results. According to this analysis, the protein array works at least as well or better using spotted antigens as compared to spotted antibodies.

|  | Antibody array | | | | Antigen array | | |
| --- | --- | --- | --- | --- | --- | --- | --- |
| Antibody/antigen | ++ | + | − | Part. conc. limit | ++ | + | − |
| Anti-AIM-1 | x | | | 1.00E−06 | x | | |
| Anti-HCG | x | | | | x | | |
| Anti-MAP4 | x | | | | x | | |
| Anti-Per2 | x | | | | x | | |
| Anti-Flag (new) | x | | | | | | x |
| Anti-Alpha HCG | x | | | 4.00E−08 | | x | |
| Anti-Fc. IgG | x | | | 1.00E−07 | | | x |
| Anti-Flag (old) | x | | | | | | |
| Anti-Human IgG | x | | | | | | |
| Anti-Mint2 | x | | | | | x | |
| Anti-Sin | x | | | | | | x |
| Anti-SOD | x | | | | | x | |
| Anti-ABR | | x | | 6.00E−05 | x | | |
| Anti-AKAP-KL | | x | | | x | | |
| Anti-Dematin | | x | | 1.00E−04 | x | | |
| Anti-Dlg | | x | | | x | | |
| Anti-DSIF | | x | | | x | | |
| Anti-FIN13 | | x | | | x | | |
| Anti-HDAC3 | | x | | | x | | |
| Anti-HIF-1alpha | | x | | | x | | |
| Anti-ICH-IL | | x | | | x | | |
| Anti-IGF2R | | x | | | x | | |
| Anti-Kanadaptin | | x | | | x | | |
| Anti-La | | x | | | x | | |
| Anti-LAIR-1 | | x | | | x | | |
| Anti-LAP2 | | x | | | x | | |
| Anti-MEKK3 | | x | | | x | | |
| Anti-Mint1 | | x | | | x | | |
| Anti-MST3 | | x | | | x | | |
| Anti-p19 Skp1 | | x | | | x | | |
| Anti-p38 gamma | | x | | | x | | |
| Anti-Rab4 | | x | | | x | | |
| Anti-TEF-1 | | x | | | x | | |
| Anti-ZO-1 | | x | | | x | | |
| Anti-Tropomyosin | | x | | | | | |
| Anti-Alkaline phosphatase | | x | | | | x | |
| Anti-cTnI | | x | | 4.00E−04 | | x | |
| Anti-DFF45 | | x | | | | x | |
| Anti-Fibronectin | | x | | | | x | |
| Anti-GOK | | x | | | | | x |
| Anti-GS15 | | x | | | | x | |
| Anti-Insulin | | x | | | | x | |
| Anti-LAT | | x | | | | x | |
| Anti-MAD-3 | | x | | | | | |
| Anti-mGluR1 | | x | | | | x | |
| Anti-MST1 | | x | | | | x | |
| Anti-Myoglobin (ResGen) | | x | | | | x | |
| Anti-Myoglobin (Sigma) | | x | | | | | |
| Anti-Neuroglycan C | | x | | | | x | |
| Anti-PSA 2F5 | | x | | | | x | |
| Anti-PSA F5 | | x | | | | | |
| Anti-Rad50 | | x | | | | x | |
| Anti-RBC | | x | | | | | x |
| Anti-Rim | | x | | | | x | |
| Anti-ROCK-1 | | x | | | | | x |
| Anti-SRPK1 | | x | | | | | x |
| Anti-VLA-3alpha | | x | | | | | x |
| Anti-Adaptin alpha | | | x | | x | | |
| Anti-Bax | | | x | | x | | |
| Anti-Calretinin | | | x | | x | | |

-continued

| Antibody/antigen | Antibody array ++ | + | - | Part. conc. limit | Antigen array ++ | + | - |
|---|---|---|---|---|---|---|---|
| Anti-c-Cbl |  | x |  |  | x |  |  |
| Anti-Clathrin H |  | x |  |  | x |  |  |
| Anti-DEK |  | x |  |  | x |  |  |
| Anti-DGK0 |  | x |  |  | x |  |  |
| Anti-Efp |  | x |  |  | x |  |  |
| Anti-erg2 |  | x |  |  | x |  |  |
| Anti-hHR23B |  | x |  |  | x |  |  |
| Anti-Kalinin B1 |  | x |  |  | x |  |  |
| Anti-PUNTS |  | x |  |  | x |  |  |
| Anti-RNCAM |  | x |  |  | x |  |  |
| Anti-SRP54 |  | x |  |  | x |  |  |
| Anti-TFII-I |  | x |  |  | x |  |  |
| Anti-TIF2 |  | x |  |  | x |  |  |
| Anti-TSP-1 |  | x |  |  | x |  |  |
| Anti-VHR |  | x |  |  | x |  |  |
| Anti-AKAP149 |  | x |  |  |  | x |  |
| Anti-alpha acid glycoprotein (AGP) |  | x |  |  |  |  | x |
| Anti-Annexin II |  | x |  |  |  |  | x |
| Anti-ARNT1 |  | x |  |  |  | x |  |
| Anti-Brm |  | x |  |  |  |  | x |
| Anti-Calmodulin |  | x |  |  |  |  | x |
| Anti-Calnexin |  | x |  |  |  |  | x |
| Anti-CaM K IV |  | x |  |  |  | x |  |
| Anti-CAS |  | x |  |  |  |  |  |
| Anti-CLA-1 |  | x |  |  |  |  | x |
| Anti-CRP |  | x |  |  |  |  | x |
| Anti-Cyclin A |  | x |  |  |  |  |  |
| Anti-DNA pol delta |  | x |  |  | x |  |  |
| Anti-elF-5 |  | x |  |  | x |  |  |
| Anti-ERp72 |  | x |  |  | x |  |  |
| Anti-ESA |  | x |  |  |  |  | x |
| Anti-G3VP |  | x |  |  | x |  |  |
| Anti-Gelsolin |  | x |  |  | x |  |  |
| Anti-Hsp70 |  | x |  |  |  |  | x |
| Anti-Hsp90 |  | x |  |  |  |  | x |
| Anti-IAK-1 |  | x |  |  | x |  |  |
| Anti-IQGAP1 |  | x |  |  |  |  | x |
| Anti-KAP3A |  | x |  |  |  |  | x |
| Anti-Ki-67 |  | x |  |  |  |  | x |
| Anti-LRP |  | x |  |  |  |  | x |
| Anti-MEK5 |  | x |  |  |  |  | x |
| Anti-Neurabin |  | x |  |  | x |  |  |
| Anti-Numb |  | x |  |  | x |  |  |
| Anti-PARP |  | x |  |  | x |  |  |
| Anti-Pax-5 |  | x |  |  |  |  | x |
| Anti-PDI |  | x |  |  |  |  | x |
| Anti-PI3-K p170 |  | x |  |  | x |  |  |
| Anti-rSec8 |  | x |  |  | x |  |  |
| Anti-SIRPalphal |  | x |  |  |  |  | x |
| Anti-Smad4 |  | x |  |  |  |  | x |
| Anti-TAF-172 |  | x |  |  |  |  | x |
| Anti-TIAR |  | x |  |  | x |  |  |
| Anti-Transportin |  | x |  |  |  |  | x |
| Anti-Utrophin |  | x |  |  |  |  | x | it is apparent from the above experimental data and descriptions that the subject methods provide a useful method for constructing a microarray comprising immobilized polypeptides. The polypeptides retain the binding specificity, and are useful in the detection and quantitation of ligands that bind to polypeptides, including proteins and fragments thereof, peptides, nucleic acids, factors and co-factors, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A microarray of discrete polypeptides on a slide, wherein each polypeptide is of at least 50 amino acids in length, wherein said microarray comprises 1000 or more discrete regions of distinct polypeptide per cm$^2$ of slide wherein discrete regions have a diameter of from 20 to 200 μm, produced by the method of:

(a) loading an aqueous solution of a selected polypeptide of at least 50 amino acids in length in a reagent-dispensing device having an elongate capillary channel adapted to hold a quantity of the reagent solution and having a tip region at which the solution in the channel forms a meniscus, (b) tapping the tip of the dispensing device against a surface of a planar solid support at a defined position, with an impulse effective to break the meniscus in the capillary channel and deposit a selected volume between 0.002 and 2 nl of solution on the surface of the planar solid support, wherein said planar solid support comprises a cationic film which binds said polypeptide, and (c) repeating steps (a) and (b) until said microarray is formed.

2. A microarray of discrete polypeptides on a slide, wherein each polypeptide is of at least 50 amino acids in length and wherein said microarray comprises 1000 or more discrete regions of distinct polypeptide per $cm^2$ of slide, and wherein discrete regions have a diameter of from 20 to 200 µm, wherein said slide comprises a cationic film which binds said polypeptide.

* * * * *

UNITED STATES PATENT AND TRADEMARK OFFICE
CERTIFICATE OF CORRECTION

PATENT NO. : 7,615,368 B1  
APPLICATION NO. : 09/550303  
DATED : November 10, 2009  
INVENTOR(S) : Brown et al.

Page 1 of 1

It is certified that error appears in the above-identified patent and that said Letters Patent is hereby corrected as shown below:

Column 1:

Insert at line 18:

-- FEDERALLY-SPONSORED RESEARCH OR DEVELOPMENT  
This invention was made with Government support under contracts CA077097, and CA085129 awarded by the National Institutes of Health. The Government has certain rights in this invention. --

Signed and Sealed this  
First Day of January, 2013

David J. Kappos  
*Director of the United States Patent and Trademark Office*